United States Patent
Shen et al.

(10) Patent No.: US 11,377,650 B2
(45) Date of Patent: Jul. 5, 2022

(54) POLYPEPTIDES HAVING D-PSICOSE 3 EPIMERASE ACTIVITY AND POLYNUCLEOTIDES ENCODING SAME

(71) Applicant: Novozymes A/S, Bagsvaerd (DK)

(72) Inventors: Xinyu Shen, Wake Forest, NC (US); Randall Scott Deinhammer, Wake Forest, NC (US); James Ron Huffman, Wake Forest, NC (US); Kendra Stallings, Wake Forest, NC (US); Tine Hoff, Holte (DK); Jesper Salomon, Holte (DK); Anne Goldbech Olsen, Valby (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/638,191

(22) PCT Filed: Aug. 30, 2018

(86) PCT No.: PCT/EP2018/073317
§ 371 (c)(1),
(2) Date: Feb. 11, 2020

(87) PCT Pub. No.: WO2019/043088
PCT Pub. Date: Mar. 7, 2019

(65) Prior Publication Data
US 2020/0362330 A1 Nov. 19, 2020

Related U.S. Application Data

(60) Provisional application No. 62/552,746, filed on Aug. 31, 2017.

(51) Int. Cl.
*C12N 9/90* (2006.01)
*C12P 19/02* (2006.01)
*C12P 19/24* (2006.01)

(52) U.S. Cl.
CPC ............... *C12N 9/90* (2013.01); *C12P 19/02* (2013.01); *C12P 19/24* (2013.01); *C12Y 501/03* (2013.01)

(58) Field of Classification Search
None
See application file for complete search history.

(56) References Cited

U.S. PATENT DOCUMENTS

2018/0112244 A1* 4/2018 Venkitasubramanian ................... C12P 19/24

FOREIGN PATENT DOCUMENTS

| EP | 3135762 A1 | 3/2017 |
| WO | 2015/099256 A1 | 7/2015 |
| WO | 2016/191267 A1 | 12/2016 |
| WO | WO-2016191267 A1 * | 12/2016 ............. C12P 19/02 |

OTHER PUBLICATIONS

GenBank, Accession No. NZ_CABKQX010000002, 2020, www.ncbi.nlm.gov. (Year: 2020).*
Chan et al., Protein Cell, vol. 3, No. 2, pp. 123-131 (2012).
Choi et al., Appl. Environ. Microbiol., vol. 77, No. 20, pp. 7316-7320 (2011).
Jia et al., Appl. Microbiol. Biotechnol., vol. 98, No. 2, pp. 717-725 (2014).
Kim et al., J. Mol. Biol., vol. 361, No. 5, pp. 920-931 (2006).
Kim et al., Biotechnol. Lett., vol. 32, No. 1, pp. 113-118 (2010).
Kim et al., Biotechnol. Lett., vol. 32, No. 2, pp. 261-268 (2010).
Mu et al., Journal of Agricultural and Food Chemistry, vol. 59, No. 14, pp. 7785-7792 (2011).
Mu et al., Biotechnol. Lett., vol. 35, No. 9, pp. 1481-1486 (2013).
Oh et al., World J. Microbiol. Biotechnol., vol. 23, No. 4, pp. 559-563 (2007).
Willsch et al., Fuel and Energy Abstracts, vol. 37, No. 2, p. 84, abstract No. 96/01208 (1996).
Zhang et al., Journal of Agricultural and Food Chemistry, vol. 61, No. 47, pp. 11468-11476 (2013).

* cited by examiner

*Primary Examiner* — Robert B Mondesi
*Assistant Examiner* — Todd M Epstein
(74) *Attorney, Agent, or Firm* — David A. Fazzolare

(57) ABSTRACT

The present invention relates to isolated polypeptides having D-psicose 3-epimerase activity and polynucleotides encoding the polypeptides. The invention also relates to nucleic acid constructs, vectors, and host cells comprising the polynucleotides as well as methods of producing and using the polypeptides.

19 Claims, 2 Drawing Sheets
Specification includes a Sequence Listing.

SEQUENCE LISTING

```
<160> NUMBER OF SEQ ID NOS: 8

<210> SEQ ID NO 1
<211> LENGTH: 873
<212> TYPE: DNA
<213> ORGANISM: Unknown
<220> FEATURE:
<223> OTHER INFORMATION: Unidentified microorganism

<400> SEQUENCE: 1
atgaaatacg gaatctacta cgcctattgg gaagacaagt gggaagcgga ctacttcaag      60
tacatcgaga aggtcgccaa gctcggcttc gacttcctgg agatcgcctg cacgccgatc     120
aacggctatt ccaagcagac gctgaaggac ctgcgccagg cggcgaagga caacggcatc     180
ttcctgacgg ccggtcacgg accgaacgcc gaccagaacc ttgcctcgcc ggacgcggct     240
gtccgcaaga acgcgaagaa gttcttcacg acgcttctca agaacctcga gatcctcgac     300
```

```
atccactcga tcggcggcgg catctacagc tactggccgg tggactactc gaagccgatc    360
gacaagaagg gcgactgggc gcgctccgtg aagggcgtgc gcgagatggg caaggtggct    420
caggactgcg gcgtcgacta ctgcctggag gtcctgaacc gcttcgaggg ttatctgctc    480
aacacggccg ccgaaggcgt gaagttcgtg aaagaggtgg acgtgccgtc cgtcaaggtc    540
atgctcgata cgttccacat gaacatcgag gaggactcga tcggcggagc gattcgctcg    600
accaaggggc tgctcggcca cttccacacg ggcgagtgca accgtcgcgt gccgggccgc    660
ggccgcacgc cgtggcacga gatcgcctgc gcgctcaagg acatcggcta caagggcaac    720
gtctgcatgg agccgttcgt tcggatgggc ggcaaggtcg gcgaggacat caaggtctgg    780
cgcgaactcg aacccggcat tccgaggcg aagatggatg cggacgcgaa ggcggcgctc    840
gacttcgaga ggatcgtgat ggagaaggtt tga                                 873
```

```
<210> SEQ ID NO 2
<211> LENGTH: 290
<212> TYPE: PRT
<213> ORGANISM: Unknown
<220> FEATURE:
<223> OTHER INFORMATION: Unidentified microorganism

<400> SEQUENCE: 2

Met Lys Tyr Gly Ile Tyr Tyr Ala Tyr Trp Glu Asp Lys Trp Glu Ala
1               5                   10                  15

Asp Tyr Phe Lys Tyr Ile Glu Lys Val Ala Lys Leu Gly Phe Asp Phe
                20                  25                  30

Leu Glu Ile Ala Cys Thr Pro Ile Asn Gly Tyr Ser Lys Gln Thr Leu
            35                  40                  45

Lys Asp Leu Arg Gln Ala Ala Lys Asp Asn Gly Ile Phe Leu Thr Ala
        50                  55                  60

Gly His Gly Pro Asn Ala Asp Gln Asn Leu Ala Ser Pro Asp Ala Ala
65                  70                  75                  80

Val Arg Lys Asn Ala Lys Lys Phe Phe Thr Thr Leu Leu Lys Asn Leu
                85                  90                  95

Glu Ile Leu Asp Ile His Ser Ile Gly Gly Ile Tyr Ser Tyr Trp
            100                 105                 110

Pro Val Asp Tyr Ser Lys Pro Ile Asp Lys Lys Gly Asp Trp Ala Arg
        115                 120                 125

Ser Val Lys Gly Val Arg Glu Met Gly Lys Val Ala Gln Asp Cys Gly
    130                 135                 140

Val Asp Tyr Cys Leu Glu Val Leu Asn Arg Phe Glu Gly Tyr Leu Leu
145                 150                 155                 160

Asn Thr Ala Ala Glu Gly Val Lys Phe Val Lys Glu Val Asp Val Pro
                165                 170                 175

Ser Val Lys Val Met Leu Asp Thr Phe His Met Asn Ile Glu Glu Asp
            180                 185                 190

Ser Ile Gly Gly Ala Ile Arg Ser Thr Lys Gly Leu Leu Gly His Phe
        195                 200                 205

His Thr Gly Glu Cys Asn Arg Arg Val Pro Gly Arg Gly Arg Thr Pro
    210                 215                 220

Trp His Glu Ile Ala Cys Ala Leu Lys Asp Ile Gly Tyr Lys Gly Asn
225                 230                 235                 240

Val Cys Met Glu Pro Phe Val Arg Met Gly Gly Lys Val Gly Glu Asp
                245                 250                 255
```

Ile Lys Val Trp Arg Glu Leu Glu Pro Gly Ile Ser Glu Ala Lys Met
            260                 265                 270

Asp Ala Asp Ala Lys Ala Ala Leu Asp Phe Glu Arg Ile Val Met Glu
        275                 280                 285

Lys Val
    290

<210> SEQ ID NO 3
<211> LENGTH: 870
<212> TYPE: DNA
<213> ORGANISM: Unknown
<220> FEATURE:
<223> OTHER INFORMATION: Unidentified microorganism

<400> SEQUENCE: 3

| | | |
|---|---|---|
| atgaagtttg gaacctattt tgcctattgg gaaaaagact gggatacgga ttatattaag | 60 |
| tatgtaaaaa aagttgccga cctgggcttt gatgttttag aagtaggagc tgcagggatt | 120 |
| gttaatatgt ctgatgaaca attatttgct ttaaagtctg aagcggagaa attcaatatt | 180 |
| actttaacag ccgggattgg tcttccgaag gaatatgatg tttcttctct agatgaagat | 240 |
| gtccgacaga tggaattgc ttttatgaaa agaattttag acgcattata taaagccggc | 300 |
| atacatgcaa tcggcggaac aatctattct tattggcctg ccgattatac ttctcctata | 360 |
| aacaaaccag aagttcgaaa acaaagcatt aaaagtatga agaattggc tgattatgca | 420 |
| gctcagtata atatcacttt gctggtggaa acactaaacc gatttgagca gttttaatt | 480 |
| aatgatgcaa agaagctgt cgcctttgta aagatatta ataaagagaa tgttaaggtc | 540 |
| atgttagata gttttcatat gaacattgag gaagattata ttggggatgc gatccgctat | 600 |
| acaggtgaat atttagggca ttccatatc ggagaatgca atcgcaaagt gcctggcaaa | 660 |
| ggtcatatgc cttgggcaga aattggacag gctcttcggg atattaatta caatggatgc | 720 |
| gtcgtcatgg aaccatttgt tcgtacaggt ggggttgtag gatcagatat aagagtctgg | 780 |
| agagatcttt ccgaaaatgc agatgatgct aaattagatg cagatattaa agaatctctt | 840 |
| gaatttatta aaaacgagtt tttaaaatag | 870 |

<210> SEQ ID NO 4
<211> LENGTH: 289
<212> TYPE: PRT
<213> ORGANISM: Unknown
<220> FEATURE:
<223> OTHER INFORMATION: Unidentified microorganism

<400> SEQUENCE: 4

Met Lys Phe Gly Thr Tyr Phe Ala Tyr Trp Glu Lys Asp Trp Asp Thr
1               5                   10                  15

Asp Tyr Ile Lys Tyr Val Lys Lys Val Ala Asp Leu Gly Phe Asp Val
            20                  25                  30

Leu Glu Val Gly Ala Ala Gly Ile Val Asn Met Ser Asp Glu Gln Leu
        35                  40                  45

Phe Ala Leu Lys Ser Glu Ala Glu Lys Phe Asn Ile Thr Leu Thr Ala
    50                  55                  60

Gly Ile Gly Leu Pro Lys Glu Tyr Asp Val Ser Ser Leu Asp Glu Asp
65                  70                  75                  80

Val Arg Gln Asn Gly Ile Ala Phe Met Lys Arg Ile Leu Asp Ala Leu
                85                  90                  95

Tyr Lys Ala Gly Ile His Ala Ile Gly Gly Thr Ile Tyr Ser Tyr Trp
            100                 105                 110

```
Pro Ala Asp Tyr Thr Ser Pro Ile Asn Lys Pro Glu Val Arg Lys Gln
        115                 120                 125

Ser Ile Lys Ser Met Lys Glu Leu Ala Asp Tyr Ala Ala Gln Tyr Asn
    130                 135                 140

Ile Thr Leu Leu Val Glu Thr Leu Asn Arg Phe Glu Gln Phe Leu Ile
145                 150                 155                 160

Asn Asp Ala Lys Glu Ala Val Ala Phe Val Lys Asp Ile Asn Lys Glu
                165                 170                 175

Asn Val Lys Val Met Leu Asp Ser Phe His Met Asn Ile Glu Glu Asp
            180                 185                 190

Tyr Ile Gly Asp Ala Ile Arg Tyr Thr Gly Tyr Leu Gly His Phe
        195                 200                 205

His Ile Gly Glu Cys Asn Arg Lys Val Pro Gly Lys Gly His Met Pro
    210                 215                 220

Trp Ala Glu Ile Gly Gln Ala Leu Arg Asp Ile Asn Tyr Asn Gly Cys
225                 230                 235                 240

Val Val Met Glu Pro Phe Val Arg Thr Gly Val Val Gly Ser Asp
                245                 250                 255

Ile Arg Val Trp Arg Asp Leu Ser Glu Asn Ala Asp Asp Ala Lys Leu
        260                 265                 270

Asp Ala Asp Ile Lys Glu Ser Leu Glu Phe Ile Lys Asn Glu Phe Leu
        275                 280                 285

Lys
```

<210> SEQ ID NO 5
<211> LENGTH: 870
<212> TYPE: DNA
<213> ORGANISM: Artificial Sequence
<220> FEATURE:
<223> OTHER INFORMATION: Artificial DNA Sequence

<400> SEQUENCE: 5

```
atgaagtatg gcatctacta tgcatactgg gaggacaaat gggaggctga ctatttcaaa    60
tacatcgaga aagttgcaaa acttggtttc gacttccttg agatcgcgtg cacaccaatc   120
aacggatatt ctaaacaaac tcttaaggac cttcgccaag ctgcgaaaga acaacggcatc   180
tttcttactg ctggccatgg tccgaacgct gaccaaaacc ttgcttctcc ggacgcagct   240
gttcgcaaaa acgcgaagaa attcttcacg acacttctta gaaccttga  gatcttagac    300
atccactcta tcggtggcgg aatctattca tactggcctg ttgactactc taaacctatc   360
gacaaaaagg gcgactgggc tcgctctgtt aaaggcgtac gcgagatggg caaagtagct   420
caagactgtg gcgttgacta ttgccttgag gtacttaacc gcttcgaggg ctaccttctt   480
aacactgcag ctgagggcgt taagtttgtt aaagaggttg acgtaccatc tgttaaagtt   540
atgttagaca cattccacat gaacatcgag gaggactcta ttggtggcgc aatccgctca   600
actaagggcc ttcttggcca tttttcatact ggcgagtgta atcgtcgcgt tcctggtcgt   660
ggtcgcactc catggcatga gatcgcttgc gctcttaaag acatcggcta caaaggcaac   720
gtttgtatgg agccttttgt acgcatgggt ggcaaagttg gcgaggacat caaagtttgg   780
cgtgagcttg agcctggcat ctctgaggcc aaaatggacg cagacgcaaa agcagctctt   840
gacttcgagc gcatcgttat ggagaaggta                                    870
```

<210> SEQ ID NO 6
<211> LENGTH: 867

```
<212> TYPE: DNA
<213> ORGANISM: Artificial Sequence
<220> FEATURE:
<223> OTHER INFORMATION: Artificial DNA Sequence

<400> SEQUENCE: 6
atgaaattcg gcacttactt cgcttactgg gagaaggact gggacacgga ctacatcaag      60
tacgtaaaga aggttgctga ccttggcttc gacgttcttg aggtaggcgc tgcaggcatc     120
gttaacatga gcgacgagca acttttcgca cttaagtctg aggctgagaa gttcaacatc     180
acacttacag ctggcatcgg ccttcctaag gagtatgacg ttagcagcct tgacgaggac     240
gtacgccaga acggcatcgc tttcatgaag cgcatccttg acgcacttta caaggctggc     300
atccacgcga ttggtggcac tatctactct tattggcctg cagactacac atctcctatc     360
aacaaacctg aggtacgcaa acaatcaatc aagtctatga aggagcttgc tgactatgct     420
gctcaataca acatcactct tcttgttgag actcttaacc gctttgagca gtttcttatc     480
aacgacgcaa aggaggctgt tgcgttcgta aaggacatca acaaggagaa cgttaaggtt     540
atgcttgact ctttccacat gaacatcgag gaggactaca tcggcgacgc aatccgctac     600
actggcgagt accttggcca cttccatatc ggcgagtgta accgcaaagt tccaggcaag     660
ggccatatgc cttgggcaga gatcggccaa gcgcttcgcg acatcaacta taacggctgc     720
gttgttatgg agccatttgt tcgcactggt ggcgtagtag gcagcgacat ccgcgtatgg     780 cgtgaccta gcgagaacgc ggacgacgct aagcttgacg ctgacatcaa ggagtcactt     840
gagttcatca agaacgagtt ccttaag                                         867

<210> SEQ ID NO 7
<211> LENGTH: 29
<212> TYPE: DNA
<213> ORGANISM: Artificial Sequence
<220> FEATURE:
<223> OTHER INFORMATION: Artificial Primer

<400> SEQUENCE: 7
gagctctata aaaatgagga gggaaccga                                        29

<210> SEQ ID NO 8
<211> LENGTH: 27
<212> TYPE: DNA
<213> ORGANISM: Artificial Sequence
<220> FEATURE:
<223> OTHER INFORMATION: Artificial Primer

<400> SEQUENCE: 8
catcatcacc atcaccacta aacgcgt                                          27
```

POLYPEPTIDES HAVING D-PSICOSE 3 EPIMERASE ACTIVITY AND POLYNUCLEOTIDES ENCODING SAME

CROSS-REFERENCE TO RELATED APPLICATIONS

This application is a 35 U.S.C. 371 national application of international application no. PCT/EP2018/073317 filed Aug. 30, 2018, which claims priority or the benefit under 35 U.S.C. 119 of U.S. provisional application No. 62/552,746 filed Aug. 31, 2017. The content of each application is fully incorporated herein by reference.

The contents of the electronic sequence listing created on Aug. 30, 2018, named 14207-WO-PCT ST25.txt and 11 KB in size, is hereby incorporated by reference in its entirety.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having D-psicose 3-epimerase activity and polynucleotides encoding the polypeptides. The invention also relates to nucleic acid constructs, vectors, and host cells comprising the polynucleotides as well as methods of producing and using the polypeptides.

Description of the Related Art

The monosaccharide D-psicose, also known as allulose, is an isomer of fructose. D-psicose is similar to D-fructose with regard to sweetness. However, unlike D-fructose, D-psicose is almost non-metabolizable in the human body and, thus, has a calorie value of nearly zero. Consequently, D-psicose is attractive as a dietary sweetener.

D-psicose exists naturally in very small amounts in, for example, edible mushrooms, jackfruit, wheat, and Itea plants, and is difficult to chemically synthesize.

There is a need in the art for developing a method for efficiently producing D-psicose. Interconversion between D-fructose and D-psicose by enzymatic epimerization catalyzed by psicose 3-epimerase is an attractive way for producing D-psicose.

The present invention provides polypeptides having D-psicose 3-epimerase activity and polynucleotides encoding the polypeptides.

SUMMARY OF THE INVENTION

The present invention relates to isolated polypeptides having D-psicose 3-epimerase activity selected from the group consisting of:
  (a) a polypeptide having at least 70% sequence identity to the polypeptide of SEQ ID NO: 2 or SEQ ID NO: 4;
  (b) a polypeptide encoded by a polynucleotide that hybridizes under very high stringency conditions with (i) the polypeptide coding sequence of SEQ ID NO: 1 or SEQ ID NO: 3, (ii) the cDNA sequence thereof, or (iii) the full-length complement of (i) or (ii);
  (c) a polypeptide encoded by a polynucleotide having at least 70% sequence identity to the polypeptide coding sequence of SEQ ID NO: 1 or SEQ ID NO: 3;
  (d) a variant of the polypeptide of SEQ ID NO: 2 or SEQ ID NO: 4 comprising a substitution, deletion, and/or insertion at one or more (e.g., several) positions; and
  (e) a fragment of the polypeptide of (a), (b), (c), or (d) that has D-psicose 3-epimerase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to methods for producing D-psicose, the method comprising: (a) contacting a composition comprising a polypeptide having D-psicose 3-epimerase of the present invention with D-fructose under conditions suitable for the polypeptide to convert D-fructose to D-psicose; and optionally (b) recovering the produced D-psicose.

DEFINITIONS

Figure 1:
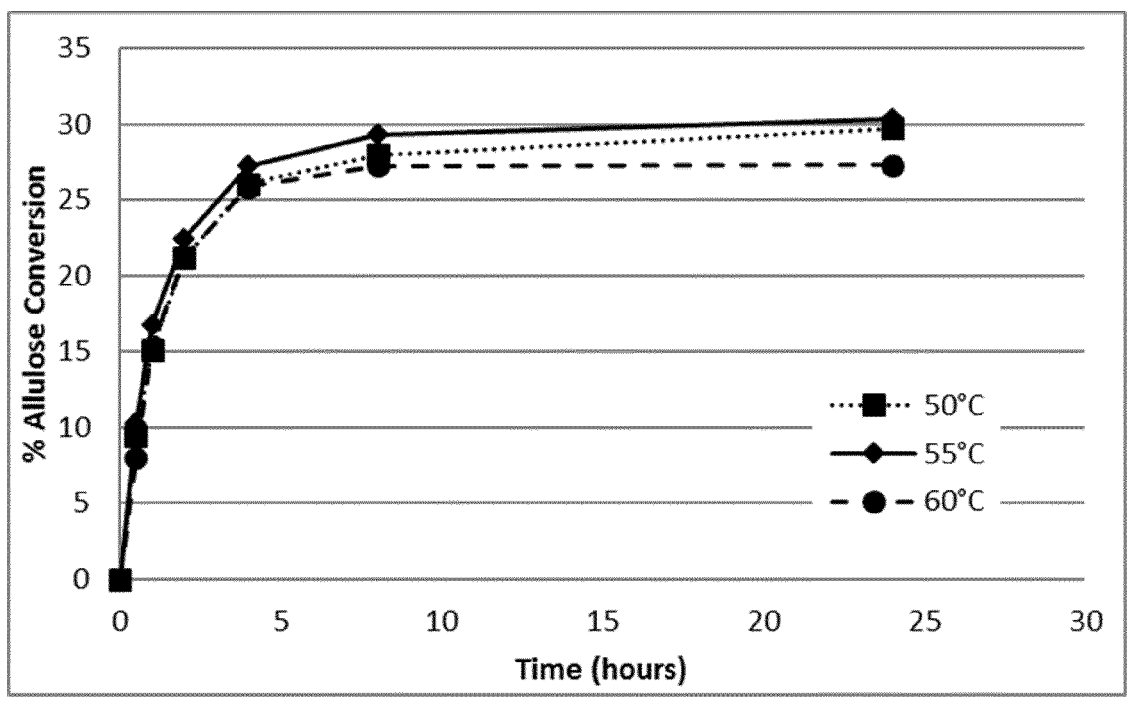
FIG. 1 shows the effect of temperature on the conversion of fructose to D-psicose by the elephant dung metagenome D-psicose 3-epimerase.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon, such as ATG, GTG, or TTG, and ends with a stop codon, such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for introducing specific restriction sites facilitating ligation of the control sequences with the coding region of the polynucleotide encoding a polypeptide.

D-psicose: The term "D-psicose" means the monosaccharide (3R,4R,5R)-1,3,4,5,6-pentahydroxyhexan-2-one. D-psicose is also known as D-allulose, allulose, psicose, or D-ribo-2-hexulose.

D-Psicose 3-epimerase: The term "D-psicose 3-epimerase" means an enzyme having D-psicose 3-epimerase activity (EC 5.1.3.30) that catalyzes the epimerization of D-psicose to D-fructose. D-psicose 3-epimerase activity can be determined according to the procedure described by Mu et al., 2011, *J. Agric. Food Chem.* 59: 7785-7792. In one aspect, the polypeptides of the present invention have at least 20%, e.g., at least 40%, at least 50%, at least 60%, at least 70%, at least 80%, at least 90%, at least 95%, or at least 100% of the D-psicose 3-epimerase activity of the polypeptide of SEQ ID NO: 2 or SEQ ID NO: 4.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a polypeptide, wherein the fragment has D-psicose 3-epimerase activity. In one aspect, a fragment contains at least 85%, at least 90%, or at least 95% of the amino acid residues of a polypeptide having. D-psicose 3-epimerase activity.

Fructose: The term "fructose" means the monosaccharide 1,3,4,5,6-pentahydroxy-2-hexanone. Fructose is also known as fruit sugar, levulose, D-fructofuranose, D-fructose, or D-arabino-hexulose.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance)

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different polypeptides (i.e., with a different C-terminal and/or N-terminal amino acid) expressed by the same polynucleotide. It is also known in the art that different host cells process polypeptides differently, and thus, one host cell expressing a polynucleotide may produce a different polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are a gap open penalty of 10, a gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Stringency conditions: The term "very low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a polypeptide coding sequence; wherein the subsequence encodes a fragment having D-psicose 3-epimerase activity. In one aspect, a subsequence contains at least 85% at least 90%, or at least 95% nucleotides of a polynucleotide encoding a polypeptide having D-psicose 3-epimerase activity.

Variant: The term "variant" means a polypeptide having D-psicose 3-epimerase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Polypeptides Having D-Psicose 3-Epimerase Activity

In an embodiment, the present invention relates to isolated polypeptides having a sequence identity to the polypeptide of SEQ ID NO: 2 or SEQ ID NO: 4 of at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have D-psicose 3-epimerase activity. In one aspect, the polypeptides differ by up to 10 amino acids, e.g., 1, 2, 3, 4, 5, 6, 7, 8, 9, or 10, from the polypeptide of SEQ ID NO: 2 or SEQ ID NO: 4.

In one aspect, the polypeptide comprises or consists of the amino acid sequence of SEQ ID NO: 2 or an allelic variant thereof; or is a fragment thereof having D-psicose 3-epimerase activity. In another aspect, the polypeptide comprises or consists of the amino acid sequence of SEQ ID NO: 2.

In another aspect, the polypeptide comprises or consists of the amino acid sequence of SEQ ID NO: 4 or an allelic variant thereof; or is a fragment thereof having D-psicose 3-epimerase activity. In another aspect, the polypeptide comprises or consists of the amino acid sequence of SEQ ID NO: 4.

In another embodiment, the present invention relates to isolated polypeptides having D-psicose 3-epimerase activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 1 or SEQ ID NO: 3 or (ii) the full-length complement thereof (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or SEQ ID NO: 4 or a fragment thereof, may be used to design nucleic acid probes to identify and clone DNA encoding polypeptides having D-psicose 3-epimerase activity from strains of different genera or species according to methods well known in the art. The probes can be used for hybridization with the genomic DNA or cDNA of a cell of interest, following standard Southern blotting procedures, to identify and isolate the corresponding gene therein. The probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having D-psicose 3-epimerase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. To identify a clone or DNA that hybridizes with SEQ ID NO: 1 or SEQ ID NO: 3, or a subsequence thereof, the carrier material is used in a Southern blot.

For purposes of the present invention, hybridization indicates that the polynucleotides hybridize to a labeled nucleic acid probe corresponding to (i) SEQ ID NO: 1 or SEQ ID NO: 3; (ii) the full-length complement thereof; or (iii) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2 or a fragment thereof. In another aspect, the nucleic acid probe is SEQ ID NO: 1. In another aspect, the nucleic acid probe is a polynucleotide that encodes the polypeptide of SEQ ID NO: 4 or a fragment thereof. In another aspect, the nucleic acid probe is SEQ ID NO: 3.

In another embodiment, the present invention relates to isolated polypeptides having D-psicose 3-epimerase activity encoded by polynucleotides having a sequence identity to the polypeptide coding sequence of SEQ ID NO: 1 or SEQ ID NO: 3 of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the polypeptide of SEQ ID NO: 2 or SEQ ID NO: 4 comprising a substitution, deletion, and/or insertion at one or more (e.g., several) positions. In one aspect, the number of amino acid substitutions, deletions and/or insertions introduced into the polypeptide of SEQ ID NO: 2 or SEQ ID NO: 4 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for D-psicose 3-epimerase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having D-Psicose 3-Epimerase Activity

A polypeptide having D-psicose 3-epimerase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is an *Agrobacterium, Arthrobacter, Bacillus, Corynebacterium, Clostridium, Desmospora, Escherichia, Pseudomonas, Rhodobacter,* or *Ruminococcus* polypeptide.

In another aspect, the *Agrobacterium* polypeptide is an *Agrobacterium tumefaciens* polypeptide.

In another aspect, the *Arthrobacter,* polypeptide is an *Arthrobacter agilis, Arthrobacter aurescens, Arthrobacter chlorophenolicus, Arthrobacter citreus, Arthrobacter crystallopoietes, Arthrobacter cumminsii, Arthrobacter globiformis, Arthrobacter luteolus, Arthrobacter nicotinovorans, Arthrobacter nitroguajacolicus, Arthrobacter pascens,* or *Arthrobacter woluwensis* polypeptide.

In another aspect, the *Bacillus* polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another aspect, the *Corynebacterium* polypeptide is a *Corynebacterium glutamicum* polypeptide.

In another aspect, the *Clostridium* polypeptide is a *Clostridium bolteae, Clostridium cellulolyticum, Clostridium hylemonae, Clostridium scindens* polypeptide.

In another aspect, the *Desmospora* polypeptide is an *Desmospora activa* polypeptide.

In another aspect, the *Escherichia* polypeptide is an *Escherichia coli* polypeptide.

In another aspect, the *Pseudomonas* polypeptide is a *Pseudomonas cichorii* or *Pseudomonas putida* polypeptide.

In another aspect, the *Rhodobacter* polypeptide is a *Rhodobacter sphaeroides* polypeptide.

In another aspect, the *Ruminococcus* polypeptide is a *Ruminococcus albus, Ruminococcus bromii, Ruminococcus callidus, Ruminococcus flavefaciens,* or *Ruminococcus gnavus* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in several culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligation activated transcription (LAT) and polynucleotide-based amplification (NASBA) may be used. The polynucleotides may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE) and *Bacillus subtilis* neutral protease (nprT).

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain enough nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in *Bacillus.*

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will depend upon the gene encoding the polypeptide and its source.

The host cell may be any cell useful in the recombinant production of a polypeptide of the present invention. In one embodiment, the host cell is a prokaryote cell.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces.* Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a Streptococcus cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide.

The present invention also relates to methods of producing a polypeptide of the present invention, comprising (a)

cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also, included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, based on when, where, and how the polypeptide is desired to be expressed (Sticklen, 2008, *Nature Reviews* 9: 433-443). For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol.*

*Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and (b) recovering the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., bacterial cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, alpha-amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, glucose isomerase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., bacterial cells) are grown to saturation, incubated under carbon-limiting conditions to allow protein synthesis. In some embodiments, the cell-killed whole broth or composition contains the spent cell culture medium, extracellular enzymes, and killed cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the amount of the polypeptide having D-psicose 3-epimerase activity has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, alpha-amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, glucose isomerase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined based on methods known in the art.

Uses

The present invention also relates to methods for producing D-psicose, the method comprising: (a) contacting a composition comprising a polypeptide having D-psicose 3-epimerase activity of the present invention with D-fructose under conditions suitable for the polypeptide having D-psicose 3-epimerase activity to convert D-fructose to D-psicose; and optionally (b) recovering the produced D-psicose.

In one aspect of the method, the D-fructose is previously produced from D-glucose by a glucose isomerase. In another aspect of the method, the D-fructose is simultaneously produced from D-glucose by a glucose isomerase. The glucose isomerase is also known as xylose isomerase (EC. 5.3.1.5). Previously produced D-fructose can be in the form of a high fructose syrup, and, in particular, a high fructose corn syrup. Such high fructose corn syrups are commercially available. Simultaneously produced D-fructose preferably uses D-glucose in the form of a glucose syrup, in particular, a glucose corn syrup.

In another aspect, D-fructose is produced by contacting starch with an alpha-amylase and a glucoamylase to release D-glucose, which is then isomerized to D-fructose by a glucose isomerase. The glucose isomerase can be immobilized (see, for example, U.S. Pat. Nos. 3,868,304, 3,982,997, 4,208,482, 4,687,742, and 5,177,005). Examples of glucose isomerases include, but are not limited to, *Streptomyces murinus* (e.g., Sweetzyme® IT Extra, Novozymes), and *Streptomyces rubiginosus* (Gensweet™ IGI, DuPont).

The reaction between the polypeptide having psicose 3-epimerase activity and D-fructose may be performed using D-fructose at a concentration of 5% to 95% (w/w), at a pH of about 5.5 to about 9.0, preferably about 6 to about 7, more preferably about 6.5, and at a temperature of about 50° C. and about 60° C., preferably about 55° C. for a suitable time. A suitable time is about 8 to about 24 hours, preferably about 10 to about 12 hours.

In another aspect, the reaction between the polypeptide having psicose 3-epimerase activity and D-fructose is performed in the presence of a divalent metal ion as a cofactor. The divalent metal ion is selected from the group consisting $Co^{2+}$, $Mg^{2+}$, $Mn^{2+}$, and $Ni^{2+}$. In a preferred aspect, the divalent metal ion is $Co^{2+}$. In another preferred aspect, the divalent metal ion is $Mg^{2+}$. In another preferred aspect, the divalent metal ion is $Mn^{2+}$. In another preferred aspect, the divalent metal ion is $Ni^{2+}$. The concentration of the metal cation cofactor can be about 0.1 to about 5 mM, for example, 1 mM, for improving the production yield of D-psicose.

The processes of the present invention can be conducted in batch or using an immobilized epimerase.

The reaction between the D-psicose 3-epimerase and D-fructose to produce D-psicose may be performed in a batch reactor.

The reaction between the D-psicose 3-epimerase and D-fructose to produce D-psicose may also be performed by immobilizing the psicose 3-epimerase on a carrier. Optionally, both glucose isomerase and D-psicose 3-epimerase can be immobilized. In an alternative, instead of immobilizing the enzyme, the microorganisms producing the enzymes are immobilized.

A carrier for immobilization may be any of the carriers known for their use in enzyme immobilization. The enzyme(s) or microorganisms can be immobilized, for example, on any suitable support, such as sodium alginate, Amberlite resin, Sephadex resin, or Duolite resin. The immobilized enzyme(s) or microorganisms can be packed into a suitable column and the glucose or fructose liquid or syrup is continuously introduced into the column. Methods for immobilizing D-psicose 3-epimerases on a support to produce D-psicose are well known to the person skilled in the art (see, for example, WO 2011/040708).

The D-psicose thus produced can be used as a dietary or pharmaceutical additive. The resulting product can be a mixture of D-fructose and D-psicose, and even a mixture of D-glucose, D-fructose and D-psicose.

The present invention is further described by the following examples that should not be construed as limiting the scope of the invention.

EXAMPLES

Media

LB medium was composed of 10 g of tryptone, 5 g of yeast extract, 5 g of NaCl, and deionized water to 1 liter.

LB plates were composed of 10 g of tryptone, 5 g of yeast extract, 5 g of NaCl, 15 g of Bacto agar, and deionized water to 1 liter.

Yeast extract-based medium was composed of 40 g of yeast extract, 1.3 g of $MgSO_4 \cdot 7H_2O$, 50 g of maltodextrin, 20 g of $NaH_2PO_4 \cdot H_2O$, 0.1 mL of antifoam, and deionized water to 1 liter.

Example 1: Identification and Characterization of D-Psicose 3-Epimerase Genes from Elephant Dung Metagenome and Anaerobic Marine Mud Metagenome A sample of elephant dung was collected from an Asian elephant at the Hamburg Zoo in Germany. A sample of marine mud was collected from a marine sediment in Manø, Denmark.

DNA isolation from the elephant dung sample was performed with a QIAamp DNA Stool Kit (Qiagen) and DNA isolation from the marine mud sample was performed with a QIAamp DNA Blood Mini Kit (Qiagen) as described in the manufacturer's protocols. Two µg of each chromosomal DNA were submitted to genome sequencing at FASTERIS SA, Switzerland. The genomes were sequenced by Illumina Sequencing. The epimerase DNA sequences were identified based on their sequence identity to a known epimerase from Clostridium cellulolyticum (GENESEQP:AZW24274).

The genomic DNA sequence and deduced amino acid sequence of the D-psicose 3-epimerase identified from the metagenome of the elephant dung sample are shown in SEQ ID NO: 1 (D448HC) and SEQ ID NO: 2 (P44DJA), respectively. The coding sequence is 873 bp including the stop codon, which is not interrupted by any introns. The encoded predicted protein is 290 amino acids. Using the SignalP 4.0 program (Petersen et al., 2011, Nature Methods 8: 785-786), no signal peptide was predicted. The predicted molecular mass is 32.57 kDa and the predicted isoelectric point is 6.68.

The genomic DNA sequence and deduced amino acid sequence of the D-psicose 3-epimerase identified from the metagenome of the anaerobic marine mud sample are shown in SEQ ID NO: 3 (D343VR) and SEQ ID NO: 4 (P43MZV), respectively. The coding sequence is 870 bp including the stop codon, which is not interrupted by any introns. The encoded predicted protein is 289 amino acids. Using the SignalP 4.0 program (Petersen et al., 2011, supra), no signal peptide was predicted. The predicted molecular mass is 32.85 kDa and the predicted isoelectric point is 4.94.

A comparative pairwise global alignment of the amino acid sequences was determined using the Needleman and Wunsch algorithm (Needleman and Wunsch, 1970, J. Mol. Biol. 48: 443-453) with a gap open penalty of 10, a gap extension penalty of 0.5, and the EBLOSUM62 matrix. The alignment showed that the deduced amino acid sequence of the D-psicose 3-epimerase identified from the metagenome of the elephant dung sample shares 67.6% sequence identity (excluding gaps) to the deduced amino acid sequence of a Clostridium cellulolyticum D-psicose 3-epimerase (GeneSeqP BBV23667) and the deduced amino acid sequence of the D-psicose 3-epimerase identified from the metagenome of the anaerobic marine mud sample shares 67.1% sequence identity (excluding gaps) to the deduced amino acid sequence of a Desmospora sp. 8437 D-psicose 3-epimerase (GeneSeqP BBE80336).

Example 2: Expression of the Elephant Dung Metagenome and Anaerobic Marine Mud Metagenome D-Psicose 3-Epimerase Genes The elephant dung metagenome and anaerobic marine mud metagenome D-psicose 3-epimerase DNA sequences (SEQ ID NO: 1 and SEQ ID NO: 3, respectively) were codon optimized for expression in Bacillus subtilis using GeneArt® GeneOptimzer® software (SEQ ID NO: 5 and SEQ ID NO: 6, respectively) and synthesized by Geneart AG. A 6×His-tag was C-terminally fused directly to each of the codon optimized genes.

The codon optimized genes were subcloned by Geneart AG into the vector C6221 described in WO 2012/025577 using the Sac I and Mlu I restrictions sites. The following sequences were added to the ends of each of the coding sequences to make cloning possible: N-terminal: gagctc-tataaaaatgaggagggaaccga (included is a Sac I restriction site; SEQ ID NO: 7) and C-terminal: catcatcaccatcac-cactaaacgcgt (included is a 6×His-tag and a Mlu I restriction site; SEQ ID NO: 8). The expression plasmids were designated 1196 for the plasmid containing the D-psicose 3-epimerase from the elephant dung metagenome and 1204 for the plasmid containing the D-psicose 3-epimerase from the marine mud metagenome.

The two expression plasmids were transformed into competent Bacillus subtilis using standard procedures. Transformants were selected on LB plates supplemented with 6 µg of chloramphenicol per mL incubated at 37° C. for 18 hours. The expression cassettes were integrated by homologous recombination into the pectate lyase locus. Several recombinant clones for each of the two gene constructs were sequenced. A recombinant clone with the correct sequence was selected for each of the two epimerase genes.

Each recombinant clone was cultivated in 500 mL baffled Erlenmeyer flasks containing 100 mL yeast extract-based medium at 30° C. for 6 days with shaking at 225 rpm. Each of the culture broths were centrifuged at 20,000×g for 20 minutes and the supernatants were carefully decanted from the pelleted material. Each supernatant was filtered using a filtration unit equipped with a 0.2 μm filter (Nalgene) to remove any cellular debris.

Example 3: Purification of the Elephant Dung Metagenome and Anaerobic Marine Mud Metagenome D-Psicose 3-Epimerases The elephant dung metagenome D-psicose 3-epimerase and anaerobic marine mud metagenome D-psicose 3-epimerase were purified from the culture supernatants prepared as described in Example 2 using the same protocol described as follows.

The pH of the supernatant was adjusted to pH 8 with 3 M Tris, left for 1 hour, and then filtered using a filtration unit equipped with a 0.2 μm filter (Nalgene). The filtered supernatant was applied to a 5 mL HisTrap™ Excel column (GE Healthcare Life Sciences) pre-equilibrated with 5 column volumes (CV) of 50 mM Tris/HCl pH 8. Unbound protein was eluted by washing the column with 8 CV of 50 mM Tris/HCl pH 8. The epimerase was eluted with 50 mM HEPES pH 7-10 mM imidazole and elution was monitored by absorbance at 280 nm. The eluted epimerase was desalted on a HiPrep™ 26/10 desalting column (GE Healthcare Life Sciences) pre-equilibrated with 3 CV of 50 mM HEPES pH 7-100 mM NaCl. The epimerase was eluted from the column using the same buffer at a flow rate of 10 mL/minute. Relevant fractions were selected and pooled based on the chromatogram and SDS-PAGE analysis using 4-12% Bis-Tris gels (Invitrogen) and 2-(N-morpholino)ethanesulfonic acid (MES) SDS-PAGE running buffer (Invitrogen). The gel was stained with InstantBlue (Novexin) and destained using miliQ water.

The concentration of the two purified enzymes was determined by absorbance at 280 nm using 1.560 and 1.451 as extinction coefficients for the elephant dung metagenome D-psicose 3-epimerase and anaerobic marine mud metagenome D-psicose 3-epimerase, respectively. The level of purity of each of the D-psicose 3-epimerases was estimated to be greater than 95% by SDS-PAGE analysis.

Example 4: Dependency of the Marine Mud Metagenome D-Psicose 3-Epimerase on Metal Ions Cofactors Mu et al., 2013, *Biotechnol. Lett.* 35: 1481-1486 disclose that some D-psicose 3-epimerases require metal ions as cofactors for epimerase activity, while other epimerases do not require a metal ion cofactor for epimerase activity or the activity of other epimerases can be enhanced by metal ions. Assays were performed to determine the dependency of different metal ion cofactors on the enzyme activity of the anaerobic marine mud metagenome D-psicose 3-epimerase.

The marine mud metagenome D-psicose 3-epimerase (3.83 mg per mL) was treated with 100 mM EDTA for 1 hour to remove any metal ions from solution followed by desalting using Zeba™ Spin Desalting Columns (ThermoFisher Scientific) and diluting the enzymes to the stock concentrations of the assay.

Each assay was conducted on a 200 μL scale with 50 grams per liter fructose as substrate. A total of 0.3 mg of EDTA treated epimerase protein per gram of fructose in 50 mM Tris buffer at pH 8 was dosed into the reaction. Metal ion stock solutions were prepared for manganese chloride tetrahydrate, cobalt(II) nitrate hexahydrate, magnesium chloride, nickel(II) chloride, ferrous chloride tetrahydrate, zinc(II) chloride, or copper(II) sulfate. These cofactors were dosed into the reaction at a final concentration of either 0.2 and 0.1 mM. Each assay was performed in duplicate in a 96-well plate.

The plates were sealed with a silicone plate sealer and placed in a thermal cycler at 55° C. for 24 hours. The assays were stopped by heating the plates in the thermal cycler at 100° C. for 10 minutes. After the assays were stopped, the plates were centrifuged at 3,000 rpm for 1 minute to remove any condensation prior to removing the plate seal.

Samples were transferred to HPLC-readable 96-well plates and analyzed for D-psicose production using a 300× 7.8 mm Aminex HPX-87C (Ca2+) column (Bio-Rad Laboratories, Inc.) at 65° C. with a flow rate of 0.7 mL/minute for 30 minutes with milliQ water as mobile phase. Standard curves of fructose, D-psicose, and glucose were run separately. After HPLC analysis, percent D-psicose produced from fructose was calculated based the peak areas relative to the standard curves. The results below are averages of duplicates.

The results shown in Table 1 demonstrate that the activity of the EDTA treated anaerobic marine mud metagenome D-psicose 3-epimerase in converting fructose to D-psicose was increased with $Co^{2+}$, $Mg^{2+}$, $Mn^{2+}$, and $Ni^{2+}$ relative to a control ("None") with the EDTA treated epimerase without any metal ion cofactor added, i.e., 24.65% and 25.12%. The presence of 0.2 or 1.0 mM metal ions yielded similar results.

TABLE 1

| % D-psicose with different metal ions as cofactor at 55° C. | | |
|---|---|---|
| Cofactor | 0.2 mM | 1.0 mM |
| $Mn^{2+}$ | 28.50 | 28.40 |
| $Co^{2+}$ | 28.79 | 28.70 |
| $Mg^{2+}$ | 28.57 | 28.71 |
| $Ni^{2+}$ | 26.88 | 19.84 |
| $Fe^{2+}$ | 16.59 | 23.13 |
| $Zn^{2+}$ | 1.79 | 0.00 |
| $Cu^{2+}$ | 1.85 | 0.74 |
| None | 24.65 | 25.12 |

Example 5: Dose Response of the Elephant Dung Metagenome and Anaerobic Marine Mud Metagenome D-Psicose 3-Epimerases on Converting Fructose to D-Psicose The ability of the elephant dung metagenome and anaerobic marine mud metagenome D-psicose 3-epimerases to convert fructose to D-psicose was assayed at different dosages of the epimerase.

Each assay was conducted on a 200 μL scale with a fructose/glucose ratio of either 42 or 95% at a total dry solids of 35% as substrate. Magnesium chloride (0.2 mM) was added as the metal ion cofactor. The reaction was conducted at pH 8 using 50 mM Tris buffer. Epimerase at 0.004, 0.011, 0.033, 0.1, 0.3 and 0.9 μg of epimerase protein per g of fructose was dosed into the assay, in quadruplicate, in a 96-well plate.

The plates were then sealed with a silicone plate sealer and incubated in a thermocycler at 50° C. for 24 hours. The assays were stopped by heating the plates in the thermocycler at 100° C. for 10 minutes. After the assays were stopped, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of four replicates.

The results shown in Table 2 demonstrate that the elephant dung metagenome D-psicose 3-epimerase produced maximum % D-psicose at a dose of 0.3 mg enzyme protein/g fructose after 24 hours at 50° C. for both 42% and 95% fructose/glucose substrates.

TABLE 2

% D-psicose at different dosages of the elephant dung metagenome D-psicose 3-epimerase from the 42% and 95% fructose/glucose substrates at 35% DS

| | Enzyme dose (µg enzyme protein/g dry solids) | | | | | |
| --- | --- | --- | --- | --- | --- | --- |
| | 0.004 | 0.011 | 0.033 | 0.1 | 0.3 | 0.9 |
| F/G = 42 | 1.70 | 3.96 | 10.00 | 18.86 | 25.30 | 27.65 |
| F/G = 95 | 1.90 | 4.68 | 12.00 | 21.52 | 26.26 | 27.94 |

The results shown in Table 3 demonstrate that the anaerobic marine mud metagenome D-psicose 3-epimerase yielded maximum % D-psicose at a dose of 0.1 mg enzyme protein/g fructose after 24 hours at 50° C. for both 42% and 95% fructose/glucose substrates.

TABLE 3

% D-psicose at different dosages of the anaerobic marine mud metagenome D-psicose 3-epimerase from the 42% and 95% fructose/glucose substrates at 35% DS

| | Enzyme dose (µg enzyme protein/g dry solids) | | | | | |
| --- | --- | --- | --- | --- | --- | --- |
| | 0.004 | 0.011 | 0.033 | 0.1 | 0.3 | 0.9 |
| F/G = 42 | 4.65 | 11.41 | 21.21 | 26.88 | 27.79 | 27.67 |
| F/G = 95 | 5.87 | 14.76 | 23.27 | 27.61 | 27.67 | 27.85 |

Example 6: Effect of Dry Solids (DS) on the Production of D-Psicose by the Elephant Dung Metagenome and Anaerobic Marine Mud Metagenome D-Psicose 3-Epimerases The performance of the elephant dung metagenome and anaerobic marine mud metagenome D-psicose 3-epimerases was evaluated as a function of 35%, 50%, and 70% dry solids of fructose:glucose at a ratio of 42%.

Each assay was composed of 35%, 50%, and 70% dry solids of fructose:glucose at a ratio of 42%, 0.2 mM magnesium chloride as the metal ion cofactor, and 0.1 mg marine mud epimerase protein per gram fructose or 0.3 mg elephant dung epimerase protein per gram fructose. The assay was conducted on a 200 µL scale at a pH of 8 using 50 mM Tris buffer. Each assay was performed in quadruplicate using 96-well plates.

The plates were sealed with a silicone plate sealer and placed in a thermocycler at 55° C. for 24 hours. The assays were stopped by heating the plates in the thermocycler at 100° C. for 10 minutes. After the assays were stopped, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of four replicates.

The results shown in Table 4 demonstrate that similar yields of D-psicose were obtained with the elephant dung metagenome D-psicose 3-epimerase when the % DS of fructose:glucose at a ratio of 42% was varied from 35% to 50% to 70%.

TABLE 4

% D-psicose as a function of dry solids percentage
Elephant dung metagenome D-psicose 3-epimerase

| | % DS | | |
| --- | --- | --- | --- |
| | 35 | 50 | 70 |
| % D-psicose | 27.14 | 27.20 | 27.65 |

The results shown in Table 5 demonstrate that similar yields of D-psicose were obtained with the marine mud metagenome D-psicose 3-epimerase when the % DS of fructose:glucose at a ratio of 42% was varied from 35% to 50% to 70%.

TABLE 5

% D-psicose as a function of dry solids percentage
Marine mud metagenome D-psicose 3-epimerase

| | DS % | | |
| --- | --- | --- | --- |
| | 35 | 50 | 70 |
| % D-psicose | 26.78 | 25.83 | 26.93 |

Example 7: Effect of Temperature on the Conversion of Fructose to D-Psicose by the Elephant Dung Metagenome and Anaerobic Marine Mud Metagenome D-Psicose 3-Epimerases A time course study was conducted to examine the effect of temperature on the conversion of fructose to D-psicose by the elephant dung metagenome and anaerobic marine mud metagenome D-psicose 3-epimerases.

This assay was performed on a 200 µL scale with 50 grams per liter fructose as the substrate. Manganese chloride was used as a metal cofactor at a final concentration of 0.2 mM. Epimerase was dosed into the reaction at a concentration of 0.5 µM. The pH was adjusted to pH 8 with 50 mM Tris buffer. Each treatment was performed in duplicate in 96-well plates. Samples were taken at time 0, 0.5, 1, 2, 4, 8, and 24 hours.

The plates were sealed with a silicone plate sealer and placed in a thermocycler at 50° C., 55° C. and 60° C. for 24 hours. The assays were stopped by heating the plates in the thermocycler at 100° C. for 10 minutes. After the assays were stopped, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of duplicates.

The results shown in Table 6 and FIG. 1 demonstrate that the elephant dung metagenome D-psicose 3-epimerase achieved conversion equilibrium after 10-12 hours at each of the temperatures of 50° C., 55° C. and 60° C.

TABLE 6

| % D-psicose during 24 hours at varied temperatures | | | |
|---|---|---|---|
| Time, hr | 50° C. | 55° C. | 60° C. |
| 0 | 0.00 | 0.00 | 0.00 |
| 0.5 | 9.42 | 10.25 | 7.96 |
| 1 | 15.11 | 16.72 | 15.30 |
| 2 | 21.19 | 22.44 | 21.25 |
| 4 | 26.04 | 27.24 | 25.87 |
| 8 | 27.99 | 29.29 | 27.23 |
| 24 | 29.71 | 30.32 | 27.32 |

Figure 2:
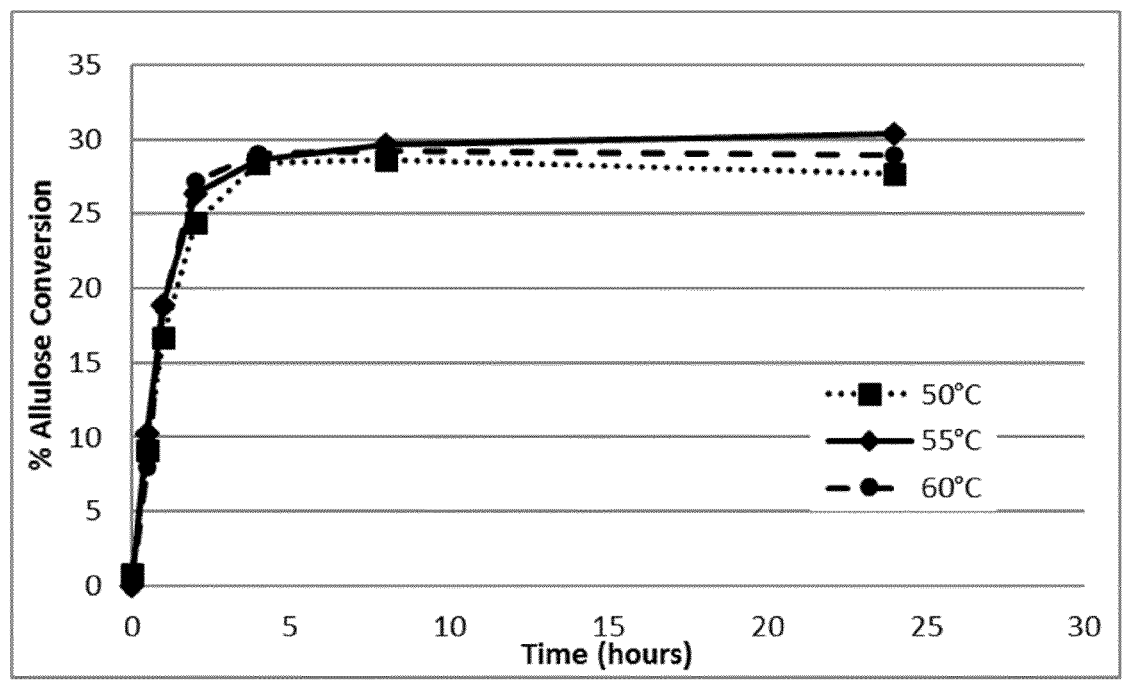
FIG. 2 shows the effect of temperature on the conversion of fructose to D-psicose by the anaerobic marine mud metagenome D-psicose 3-epimerase.

The results shown in Table 7 and FIG. 2 demonstrate that the anaerobic marine mud metagenome D-psicose 3-epimerase achieved conversion equilibrium 10-12 hours at each of the temperatures of 50° C., 55° C. and 60° C.

TABLE 7

| % D-psicose during 24 hours at varied temperatures | | | |
|---|---|---|---|
| Time, hr | 50° C. | 55° C. | 60° C. |
| 0 | 0.80 | 0.00 | 0.00 |
| 0.5 | 9.16 | 10.22 | 7.93 |
| 1 | 16.75 | 18.82 | 18.82 |
| 2 | 24.38 | 26.32 | 27.18 |
| 4 | 28.42 | 28.62 | 29.08 |
| 8 | 28.68 | 29.62 | 29.26 |
| 24 | 27.74 | 30.32 | 28.91 |

Example 8: Effect of pH and Temperature on the Activity of the Elephant Dung Metagenome and Anaerobic Marine Mud Metagenome D-Psicose 3-Epimerases The effect of pH and temperature on the activity of the elephant dung metagenome and anaerobic marine mud metagenome D-psicose 3-epimerases was determined at pHs 7.0, 7.5, 8, 8.5, and 9.0 and temperatures 50° C., 55° C., and 60° C.

This assay was performed on a 200 μL scale with 50 grams per liter fructose as the substrate. Manganese chloride was used as a metal cofactor at a final concentration of 0.2 mM. Epimerase was dosed into the reaction at 0.5 μM. The pH was adjusted to pH 7, 7.5, 8, 8.5, and 9.0 with 50 mM Tris buffer adjusted with HCl. Each treatment was performed in duplicate in 96-well plates.

Three different 96-well plates were used, one for each temperature (45° C., 55° C., or 65° C.). The solutions were mixed via pipette aspiration. The three temperature plates were sealed with a silicone plate sealer and placed in a thermocycler at either 45° C., 55° C., or 65° C. for 24 hours. The assays were stopped by heating the plates in the thermocycler at 100° C. for 10 minutes. The plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of duplicates.

The results shown in Table 8 demonstrate that the elephant dung metagenome D-psicose 3-epimerase was stable at 45° C. and 55° C. over the pH range from 7-9, each reaching maximum D-psicose yield. At 65° C., the epimerase was stable at pH 7.0.

TABLE 8

| % D-psicose | | | |
|---|---|---|---|
| | Temp (° C.) | | |
| pH | 45 | 55 | 65 |
| 7.0 | 27.6 | 29.5 | 30.4 |
| 7.5 | 28.3 | 30.3 | 24.4 |
| 8.0 | 27.5 | 29.6 | 22.5 |
| 8.5 | 27.7 | 30.5 | 21.1 |
| 9.0 | 27.2 | 29.0 | 15.0 |

The results shown in Table 9 demonstrate that the anaerobic marine mud metagenome D-psicose 3-epimerase was stable at 45° C., 55° C., and 65° C. over the pH range 7-9, each reaching maximum D-psicose yield.

TABLE 9

| % D-psicose | | | |
|---|---|---|---|
| | Temp (° C.) | | |
| pH | 45 | 55 | 65 |
| 7.0 | 28.3 | 29.9 | 32.6 |
| 7.5 | 27.1 | 30.0 | 30.9 |
| 8.0 | 28.9 | 29.9 | 30.5 |
| 8.5 | 27.9 | 30.5 | 31.1 |
| 9.0 | 27.0 | 28.2 | 29.6 |

Example 9: Effect of pH and Temperature on the Activity of the Elephant Dung Metagenome and Anaerobic Marine Mud Metagenome D-Psicose 3-Epimerases The effect of pH and temperature on the activity of the elephant dung metagenome and anaerobic marine mud metagenome D-psicose 3-epimerases was determined at pHs 5.5, 6.0, and 6.5 and temperatures 50° C., 53.8° C., 57.5° C., 62° C., 65.9° C., and 70° C.

This assay was performed on a 200 μL scale with 42% fructose:glucose as substrate at 50% total solids. The anaerobic marine mud metagenome epimerase was dosed at 0.1 mg protein per gram fructose and the elephant dung metagenome epimerase was dosed at 0.3 mg epimerase protein per gram fructose. Magnesium sulfate (0.2 mM) was used as the metal cofactor. The pH was adjusted to 5.5, 6, and 6.5 using 50 mM sodium acetate buffer.

The plate was sealed with a silicone plate sealer and placed in a thermal cycler programmed with a temperature gradient across the plate from 50° C. to 70° C. for 24 hours. The assays were stopped by heating the plates in the thermal cyclers at 100° C. for 10 minutes. After the assays were stopped, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results are averages of four replicates.

The results shown in Table 10 demonstrate that the elephant dung metagenome D-psicose 3-epimerase was stable at pH 5.5, 6.0, and 6.5 from 50 to 62° C., reaching maximum D-psicose conversion, with conversion increasing slightly with an increase in temperature.

TABLE 10

| | % D-psicose | | | | | |
|---|---|---|---|---|---|---|
| | Temp (° C.) | | | | | |
| pH | 50 | 53.8 | 57.5 | 62 | 65.9 | 70 |
| 5.5 | 27.5 | 28.4 | 28.9 | 29.3 | 25.9 | 16.3 |
| 6.0 | 27.6 | 28.4 | 28.9 | 29.7 | 28.8 | 22.9 |
| 6.5 | 27.8 | 28.4 | 29.1 | 29.6 | 29.2 | 26.4 |

The results shown in Table 11 demonstrate that the anaerobic marine mud metagenome D-psicose 3-epimerase reached maximum D-psicose conversion at pH 5.5, 6.0, and 6.5 from 50 to 62° C., with conversion increasing slightly with an increase in temperature.

TABLE 11

| | % D-psicose | | | | | |
|---|---|---|---|---|---|---|
| | Temp (° C.) | | | | | |
| pH | 50 | 53.8 | 57.5 | 62 | 65.9 | 70 |
| 5.5 | 27.2 | 27.8 | 28.5 | 28.4 | 26.2 | 19.5 |
| 6.0 | 27.6 | 28.4 | 29.1 | 29.6 | 29.1 | 26.3 |
| 6.5 | 27.7 | 28.4 | 29.3 | 29.8 | 29.7 | 28.0 |

Example 10: Kinetics of the Elephant Dung Metagenome and Anaerobic Marine Mud Metagenome D-Psicose 3-Epimerases as a Function of Various Fructose Concentrations The kinetics of the elephant dung metagenome and anaerobic marine mud metagenome D-psicose 3-epimerases in converting fructose to D-psicose was assayed by monitoring the effect of different fructose concentrations on enzyme activity.

This assay was conducted on a 200 µL scale with 50, 420, and 950 grams per liter fructose as substrate. Manganese chloride was used as a metal cofactor at a final concentration of 0.2 mM. Epimerase was dosed into this assay at a concentration of 0.33 mg epimerase protein per gram fructose. The pH was adjusted to 8 with 50 mM Tris buffer. Each assay was performed in duplicate in a 96-well plate.

The three plates were sealed with a silicone plate sealer and placed in three different thermal cyclers at either 40° C., 55° C., or 65° C. Samples were collected at 1, 2, 4, 24, 48, and 72 hours. The plates were centrifuged at 3,000 rpm for 1 minute before sampling a time point to remove any condensation prior to removing the plate seal. A 200 µL volume of each sample at the given time point was collected from the plate and transferred into a new PCR 96-well plate. The original plates were placed back in the thermal cycler to continue the assay until the next sampling time points. The PCR plates containing the sample at the specific time points were then placed in a different thermal cycler at 98° C. for 10 minutes to inactivate the enzyme. The plates containing the inactivated samples were then centrifuged at 3,000 rpm for 1 minute to remove any condensation prior to removing the plate seal.

The 420 and 950 g/L fructose samples were diluted 10× and 20×, respectively, with deionized water and transferred into HPLC-readable 96-well plates. The 50 g/L fructose samples were transferred undiluted into the HPLC plates. The plates were heat sealed and analyzed by HPLC according to Example 4 to determine percent D-psicose produced from fructose. Results below are averages of duplicates The results shown in Table 12 demonstrate percent conversion of fructose to D-psicose relative to the starting fructose concentration for the elephant dung metagenome D-psicose 3-epimerase at 40° C. The epimerase achieved maximum conversion of fructose to D-psicose with 50 and 420 g/L fructose as substrate at 40° C. in 4 hours and achieved around 66% maximum conversion even with 950 g/L fructose as substrate by 24 hours.

TABLE 12

| | % D-psicose at 40° C. | | | | |
|---|---|---|---|---|---|
| Fructose | Time point (hr) | | | | |
| Concentration | 0 | 4 | 24 | 48 | 72 |
| 50 g/L | 0 | 27.10 | 25.80 | 25.88 | 25.89 |
| 420 g/L | 0 | 28.65 | 26.14 | 26.19 | 30.06 |
| 950 g/L | 0 | 2.15 | 19.93 | 20.02 | 21.51 |

The results shown in Table 13 demonstrate percent conversion of fructose to D-psicose relative to the starting fructose concentration for the elephant dung metagenome D-psicose 3-epimerase at 55° C. The epimerase achieved maximum conversion of fructose to D-psicose with 50 and 420 g/L fructose as substrate at 55° C. for 24 hours and achieved around 70% maximum conversion even with 950 g/L fructose as substrate by 24 hours.

TABLE 13

| | % D-psicose at 55° C. | | | | |
|---|---|---|---|---|---|
| Fructose | Time point (hr) | | | | |
| Concentration | 0 | 4 | 24 | 48 | 72 |
| 50 g/L | 0 | 22.3 | 28.5 | 28.5 | 28.7 |
| 420 g/L | 0 | 25.1 | 29.0 | 29.0 | 29.2 |
| 950 g/L | 0 | 10.5 | 22.7 | 23.6 | 23.2 |

The results shown in Table 14 demonstrate percent conversion of fructose to D-psicose relative to the starting fructose concentration for the elephant dung metagenome D-psicose 3-epimerase at 65° C. Increasing the substrate concentration increased the thermostability of the epimerase as seen where 30% conversion was reached at 65° C. with 420 g/L fructose after only 4 hours.

TABLE 14

| | % D-psicose at 65° C. (%) | | | | |
|---|---|---|---|---|---|
| Fructose | Time point (hr) | | | | |
| Concentration | 0 | 4 | 24 | 48 | 72 |
| 50 g/L | 0 | 12.96 | — | 28.4 | 23.1 |
| 420 g/L | 0 | 29.72 | 30.5 | 30.4 | 30.3 |
| 950 g/L | 0 | 3.61 | 25.8 | 24.8 | 19.3 |

The results shown in Table 15 demonstrate percent conversion of fructose to D-psicose relative to the starting fructose concentration for the anaerobic marine mud metagenome D-psicose 3-epimerase at 40° C. Maximum D-psicose was reached at 50 and 420 g/L fructose at 40° C. after 4 hours.

TABLE 15

| % D-psicose at 40° C. (%) | | | | | |
|---|---|---|---|---|---|
| Fructose | Time point (hr) | | | | |
| Concentration | 0 | 4 | 24 | 48 | 72 |
| 50 g/L | 0 | 28.21 | 25.79 | — | 25.82 |
| 420 g/L | 0 | 28.68 | 26.23 | 26.13 | 22.70 |
| 950 g/L | 0 | 6.49 | 20.23 | 21.31 | 21.62 |

The results shown in Table 16 demonstrate percent conversion of fructose to D-psicose relative to the starting fructose concentration for the anaerobic marine mud metagenome D-psicose 3-epimerase at 55° C. Maximum D-psicose was reached at 50 and 420 g/L fructose at 55° C. after 24 hours.

TABLE 16

| % D-psicose at 55° C. | | | | | |
|---|---|---|---|---|---|
| Fructose | Time point (hr) | | | | |
| Concentration | 0 | 4 | 24 | 48 | 72 |
| 50 g/L | 0 | 24.9 | 28.3 | 28.4 | 28.6 |
| 420 g/L | 0 | 26.5 | 29.1 | 29.0 | 28.9 |
| 950 g/L | 0 | 12.1 | 23.7 | 27.3 | 25.8 |

The results shown in Table 17 demonstrate percent conversion of fructose to D-psicose relative to the starting fructose concentration for the anaerobic marine mud metagenome D-psicose 3-epimerase at 55° C. Maximum D-psicose was reached after 4 hours at 65° C. for 50 and 420 g/L fructose and after 24 hours for 950 g/L fructose.

TABLE 17

| % D-psicose at 65° C. | | | | | |
|---|---|---|---|---|---|
| Fructose | Time point (hr) | | | | |
| Concentration | 0 | 4 | 24 | 48 | 72 |
| 50 g/L | 0 | 29.76 | 25.4 | 30.1 | 30.2 |
| 420 g/L | 0 | 30.16 | 30.7 | 30.5 | 30.4 |
| 950 g/L | 0 | 15.66 | 29.5 | 29.1 | 30.1 |

Example 11: Temperature Inactivation of the Elephant Dung Metagenome and Anaerobic Marine Mud Metagenome D-Psicose 3-Epimerases Residual activity of the elephant dung metagenome and anaerobic marine mud metagenome D-psicose 3-epimerases was determined after subjecting the epimerases to a range of temperatures.

Each epimerase was exposed to temperatures ranging from 60-85° C. for 30 and 60 minutes and 100° C. for 10 minutes as a negative control. A positive control with no temperature treatment was also included.

A thermal cycler was used in this assay with a programmed temperature gradient from 60-85° C. There was one plate for each of the inactivation incubation periods of 30 and 60 minutes in the thermal cycler. Separately, the diluted enzyme was added to another PCR 96-well plate and incubated in the thermal cycler at 100° C. for 10 minutes. After all the epimerase samples had been subjected to the appropriate inactivation times and temperatures, they were all combined in a 96-well plate. An untreated epimerase sample was also included in this plate as a positive control. The samples were then assayed for epimerase activity as described below to determine residual epimerase activity.

This assay was conducted on a 200 µL scale with 50 grams per liter fructose as substrate. Manganese chloride was used as a metal cofactor at a final concentration of 0.2 mM. Epimerase was dosed into the assay at and 0.5 µM. The pH was adjusted to 8 with 50 mM Tris buffer. Each assay was performed in duplicate in a 96-well plate.

Silicone lids were applied to the PCR plates and the plates were placed in the thermal cycler at 55° C. for 24 hours. After the reactions ended, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of duplicates.

The results shown in Table 18 demonstrate the percent of D-psicose produced after inactivation relative to the starting fructose concentration for the elephant dung metagenome D-psicose 3-epimerase. The epimerase was completely inactivated after incubation at 80.4° C. for 30 minutes.

TABLE 18

| Residual Epimerase Activity (% D-psicose) | | |
|---|---|---|
| | Inactivation Time (min) | |
| Temp (° C.) | 30 | 60 |
| none | 30.3 | |
| 61.0 | 25.8 | 22.7 |
| 65.7 | 20.8 | 16.1 |
| 70.4 | 13.5 | 7.7 |
| 75.8 | 2.3 | 0.7 |
| 80.4 | 0 | 0 |
| 85.0 | 0 | 0 |
| 100, 10 minutes | 0 | |

The results shown in Table 19 demonstrate the percent of D-psicose produced after inactivation relative to the starting fructose concentration for the anaerobic marine mud metagenome D-psicose 3-epimerase. The epimerase was completely inactivated after incubation at 80.4° C. for 30 minutes

TABLE 19

| Residual Epimerase Activity (% D-psicose conversion) | | |
|---|---|---|
| | Inactivation Time (min) | |
| Temp (° C.) | 30 | 60 |
| none | 28.5 | |
| 61.0 | 28.9 | 28.2 |
| 65.7 | 28.6 | 28.1 |
| 70.4 | 7.3 | 4.4 |
| 75.8 | 1.6 | 0.5 |
| 80.4 | 0 | 0 |
| 85.0 | 0 | 0 |
| 100, 10 minutes | 0 | |

Example 12: pH Inactivation of the Elephant Dung Metagenome and Anaerobic Marine Mud Metagenome D-Psicose 3-Epimerases Residual activity of the elephant dung metagenome and anaerobic marine mud metagenome D-psicose 3-epimerases was determined after incubation at pHs ranging from 1.5 to 8.0.

The correct amount of HCl was added to the enzyme in the PCR plate and allowed to sit for 10 minutes with gentle shaking. Then, 25 µL of the correct concentration of NaOH was added to neutralize the solutions. The PCR plate containing pH-inactivated enzymes was then subjected to the epimerase reaction protocol.

A 100 µL volume of the reaction buffer at 100 g/L fructose was added to 100 µL of previously inactivated epimerase solution in the PCR plates. The combined solution containing 50 g/L fructose with 0.5 µM epimerase was mixed via pipette aspiration. The final concentration of the stock reaction buffer was 100 g/L fructose, 50 mM Tris, and 0.2 mM $MnCl_2$.

Silicone lids were applied to the PCR plates and the plates were placed in the thermal cycler at 55° C. for 24 hours. The assays were stopped by heating at 100° C. for 10 minutes in the thermal cycler. After the assays ended, the plates were centrifuged at 3,000 rpm for 1 minute to remove any condensation prior to removing the plate seal.

Samples were transferred to HPLC-readable 96-well plates and analyzed by HPLC according to Example 4 to determine percent D-psicose produced from fructose. The results below are averages of duplicates.

The results shown in Table 20 demonstrate % conversion of fructose to D-psicose after incubation of the elephant dung metagenome D-psicose 3-epimerase at the pHs shown in Table 20 for 10 minutes. The epimerase was inactivated by incubation at pH 2.5 for 10 minutes.

TABLE 20

Residual epimerase activity after pH inactivation

| pH | % D-psicose |
|---|---|
| 1.5 | 0.0 |
| 2.0 | 0.0 |
| 2.5 | 0.0 |
| 3.0 | 21.7 |
| 3.5 | 29.8 |
| 4.0 | 29.2 |
| 4.5 | 30.0 |
| 5.0 | 30.1 |
| 5.5 | 28.7 |
| 6.0 | 30.0 |
| 8.0 | 30.2 |

The results shown in Table 20 demonstrate % conversion of fructose to D-psicose after incubation of the anaerobic marine mud metagenome D-psicose 3-epimerase at the pHs for 10 minutes shown in Table 21. The epimerase was stable down to at least pH 1.5 after incubation for 10 minutes.

TABLE 21

Residual epimerase activity after pH inactivation

| pH | % D-psicose |
|---|---|
| 1.5 | 30.2 |
| 2.0 | 29.6 |
| 2.5 | 29.8 |
| 3.0 | 29.6 |
| 3.5 | 28.7 |
| 4.0 | 29.1 |
| 4.5 | 29.7 |
| 5.0 | 29.1 |
| 5.5 | 29.0 |
| 6.0 | 29.2 |
| 8.0 | 28.8 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

What is claimed is:

1. An isolated polynucleotide encoding an isolated polypeptide having D-psicose 3-epimerase activity, wherein the polynucleotide is operably linked to one or more heterologous control sequences that direct the production of the polypeptide in an expression host, wherein the polypeptide is selected from the group consisting of:
   (a) a polypeptide having at least 95% sequence identity to the polypeptide of SEQ ID NO: 2 or SEQ ID NO: 4;
   (b) a polypeptide encoded by a polynucleotide having at least 95% sequence identity to the polypeptide coding sequence of SEQ ID NO: 1 or SEQ ID NO: 3; and
   (c) a fragment of the polypeptide of (a) or (b) that has D-psicose 3-epimerase activity.

2. A nucleic acid construct or expression vector comprising the polynucleotide of claim 1.

3. The polynucleotide of claim 1, wherein the polypeptide has at least 97% sequence identity to the polypeptide of SEQ ID NO: 2.

4. The polynucleotide of claim 1, wherein the polypeptide has at least 99% sequence identity to the polypeptide of SEQ ID NO: 2.

5. The polynucleotide of claim 1, wherein the polypeptide has at least 97% sequence identity to the polypeptide of SEQ ID NO: 4.

6. The polynucleotide of claim 1, wherein the polypeptide has at least 99% sequence identity to the polypeptide of SEQ ID NO: 4.

7. A recombinant host cell comprising an isolated polynucleotide encoding an isolated polypeptide having D-psicose 3-epimerase activity, wherein the polynucleotide is operably linked to one or more heterologous control sequences that direct the production of the polypeptide, and wherein the polypeptide is selected from the group consisting of:
  (a) a polypeptide having at least 95% sequence identity to the polypeptide of SEQ ID NO: 2 or SEQ ID NO: 4;
  (b) a polypeptide encoded by a polynucleotide having at least 95% sequence identity to the polypeptide coding sequence of SEQ ID NO: 1 or SEQ ID NO: 3; and
  (c) a fragment of the polypeptide of (a) or (b) that has D-psicose 3-epimerase activity.

8. The host cell of claim 7, wherein the polypeptide has at least 95% sequence identity to the polypeptide of SEQ ID NO: 2.

9. The host cell of claim 7, wherein the polypeptide has at least 97% sequence identity to the polypeptide of SEQ ID NO: 2.

10. The host cell of claim 7, wherein the polypeptide has at least 99% sequence identity to the polypeptide of SEQ ID NO: 2.

11. The host cell of claim 7, wherein the polypeptide has at least 95% sequence identity to the polypeptide of SEQ ID NO: 4.

12. The host cell of claim 7, wherein the polypeptide has at least 97% sequence identity to the polypeptide of SEQ ID NO: 4.

13. The host cell of claim 7, wherein the polypeptide has at least 99% sequence identity to the polypeptide of SEQ ID NO: 4.

14. A method of producing a polypeptide having D-psicose 3-epimerase activity, comprising cultivating a recombinant host cell under conditions conducive for production of the polypeptide, wherein the recombinant host cell comprises an isolated polynucleotide encoding an isolated polypeptide having D-psicose 3-epimerase activity, wherein the polynucleotide is operably linked to one or more heterologous control sequences that direct the production of the polypeptide in the host cell, and wherein the polypeptide is selected from the group consisting of:
  (a) a polypeptide having at least 95% sequence identity to the polypeptide of SEQ ID NO: 2 or SEQ ID NO: 4;
  (b) a polypeptide encoded by a polynucleotide having at least 95% sequence identity to the polypeptide coding sequence of SEQ ID NO: 1 or SEQ ID NO: 3; and
  (c) a fragment of the polypeptide of (a) or (b) that has D-psicose 3-epimerase activity.

15. The method of claim 14, further comprising recovering the polypeptide.

16. The method of claim 14, wherein the polypeptide has at least 97% sequence identity to the polypeptide of SEQ ID NO: 2.

17. The method of claim 14, wherein the polypeptide has at least 99% sequence identity to the polypeptide of SEQ ID NO: 2.

18. The method of claim 14, wherein the polypeptide has at least 97% sequence identity to the polypeptide of SEQ ID NO: 4.

19. The method of claim 14, wherein the polypeptide has at least 99% sequence identity to the polypeptide of SEQ ID NO: 4.

* * * * *